US012150977B2

(12) United States Patent
Kiester

(10) Patent No.: US 12,150,977 B2
(45) Date of Patent: Nov. 26, 2024

(54) METHODS, APPARATUSES AND SYSTEMS FOR ADOLESCENT IDIOPATHIC SCOLIOSIS TREATMENT

(71) Applicant: Phillip Douglas Kiester, Irvine, CA (US)

(72) Inventor: Phillip Douglas Kiester, Irvine, CA (US)

(73) Assignee: Phillip Douglas Kiester, Irvine, CA (US)

( * ) Notice: Subject to any disclaimer, the term of this patent is extended or adjusted under 35 U.S.C. 154(b) by 686 days.

(21) Appl. No.: 16/877,329

(22) Filed: May 18, 2020

(65) Prior Publication Data
US 2021/0353723 A1 Nov. 18, 2021

(51) Int. Cl.
*A61K 38/48* (2006.01)
*A61B 17/16* (2006.01)
*C12N 9/64* (2006.01)
*A61B 90/00* (2016.01)
*C12N 9/52* (2006.01)

(52) U.S. Cl.
CPC ...... *A61K 38/4886* (2013.01); *A61B 17/1671* (2013.01); *C12N 9/6416* (2013.01); *C12Y 304/24003* (2016.02); *C12N 9/52* (2013.01); *C12N 9/6491* (2013.01)

(58) Field of Classification Search
CPC ............ A61K 38/4886; A61B 17/1671; A61B 2090/033; C12N 9/6416; C12Y 304/24003

USPC .......................................................... 604/22
See application file for complete search history.

(56) References Cited

U.S. PATENT DOCUMENTS

| 3,678,158 A | * | 7/1972 | Sussman | .................. | C12N 9/52 |
| | | | | | 424/94.67 |
| 2003/0158545 A1 | * | 8/2003 | Hovda | ................. | A61B 18/148 |
| | | | | | 606/49 |

OTHER PUBLICATIONS

Adams, Williams, "Lectures on the Pathology and Treatment of Lateral and Other Forms of Curvature of the Spine", J & A Churchill, second edition 1882, originally published 1865, pp. 462-463, London.
Sommerville, E.W., "Rotational Lordosis: The Development of the Single Curve", J Bone and Joint Surg, Aug. 1952; vol. 34B(3), pp. 421-427, Oxford, England.
Smith, R.M., et al., "Experimental Structural Scoliosis", JBJS-B 1987; vol. 69-B(4), p. 576-581, Leeds.

* cited by examiner

*Primary Examiner* — Phillip A Gray
(74) *Attorney, Agent, or Firm* — Workman Nydegger

(57) ABSTRACT

The METHODS, APPARATUSES AND SYSTEMS FOR ADOLESCENT IDIOPATHIC SCOLIOSIS TREATMENT (hereinafter "AIST") disclosed herein leverage the biomechanical cause of AIS in the ventral portion of the interspinous ligament to treat AIS. In various embodiments, the AIST include chemically lysing the abnormal tethering structure, thereby allowing the AIS spine to decrease its deformity with usual day-to-day activities, without bracing and without instrumented and/or fusion surgery.

8 Claims, 4 Drawing Sheets

METHODS, APPARATUSES AND SYSTEMS FOR ADOLESCENT IDIOPATHIC SCOLIOSIS TREATMENT

This application for letters patent disclosure document describes inventive aspects that include various novel innovations (hereinafter "disclosure") and contains material that is subject to copyright, and/or other intellectual property protection. The respective owners of such intellectual property have no objection to the facsimile reproduction of the disclosure by anyone as it appears in published records as well as Patent Office files and records, but otherwise reserve all rights.

FIELD

The present innovations generally address the treatment of disorders such as scoliosis, and more particularly, include METHODS, APPARATUSES AND SYSTEMS FOR ADOLESCENT IDIOPATHIC SCOLIOSIS TREATMENT.

BACKGROUND

Scoliosis is generally thought of as a lateral bending of the spine. This understanding is adequate for such conditions as scoliosis from a leg length discrepancy, intentional voluntary lateral bending, some forms of scoliosis due to trauma, or some forms of congenital scoliosis such as a unilateral failure of vertebral body segmentation (spontaneous unilateral vertebral body fusion in a child). These forms of scoliosis are indeed usually a simple lateral bending of the spine.

Adult deformity (adult onset scoliosis), neuromuscular scoliosis, some forms of congenital and early onset scoliosis, and Adolescent Idiopathic Scoliosis (AIS) are all characterized has having rotation of the vertebral bodies in addition to having a lateral bend. Adolescent Scoliosis is currently called "Idiopathic" because many physicians currently treating this disorder do not understand what the mechanical cause is for either the vertebral rotation or the lateral bending of the spine. In 1865, William Adams (Adams, W., *Lectures on the Pathology and Treatment of Lateral and Other Forms of Curvature of the Spine*. London: J & A Churchill, second edition 1882, originally published 1865) accurately described the mechanical cause for both the vertebral body rotation and the lateral bend observed in AIS. His observations resulted in the "Adams' Test," which is still the standard for school screening for AIS.

The Adams' Test is focused on the rotation of the spine, which can be clearly observed because the ribs are attached to the spine. A typical thoracic spine curve (curve in the chest area) is off to the right where the heart on the left has pushed the spine away. This forces the right chest ribs to rotate clockwise (as viewed from above) which pushes the right ribs backward away from the body (making the right ribs stick out). The left ribs will then rotate into the body, sinking them into the chest. The Adams' Test is performed by having the child stand with their back to the examiner and lean forward. This forward bending motion (flexion) compresses the disks even more, which increases the vertebral body rotation. The increased thoracic rotation makes the unilateral rib hump even more prominent. The examiner notes if the ribs on one side are higher than the other with the child bent forward. If one side of the ribs are higher than the other, the screening test for AIS is positive. The child has the AIS spinal deformity.

Scoliosis surgeons discovered over two decades ago that if they aggressively removed the facets and ligamentum flavum, the bony spinal column would "loosen up" and allow a better correction of the scoliosis deformity. These procedures are called Ponté or Smith-Peterson Osteotomies. (Osteotomy means to cut the bone.) In order to conduct these procedures, the tether between the spinous processes is also cut. The surgeon believes he is cutting and removing the ligamentum flavum. The tether is directly on top of the ligamentum, and is difficult to identify as a structure that is separate and distinct from the ligamentum. Complete removal of the ligamentum flavum is a standard part of these osteotomies. These procedures are now the standard of care when performing adolescent scoliosis instrumented corrective spine surgery. Performing these procedures adds to the operative time, but does not add significantly to the overall safety or complication rate of these scoliosis corrective surgeries.

SUMMARY

The METHODS, APPARATUSES AND SYSTEMS FOR ADOLESCENT IDIOPATHIC SCOLIOSIS TREATMENT (hereinafter "AIST") leverage the biomechanical cause of AIS in the ventral portion of the interspinous ligament to treat AIS. In various embodiments, the AIST include chemically lysing the tether or abnormal tethering structure (the ventral portion of the interspinous ligament), thereby allowing the AIS spine to decrease its deformity with usual day-to-day activities, without bracing and without instrumented and/or fusion surgery. Like a pencil standing on an eraser, the center of gravity of the human body must remain over a relatively small base of support (the feet) or it will fall over. The mechanisms which pull on the spine to stay centered over the base of support work to correct the spinal deformity once the constraining tether is released. Walking, sports, and daily life activities activate these mechanisms and accelerate the correction. Body bracing inhibits these mechanisms and slows natural deformity correction. If spinal fusion surgery becomes desired, these methods will in no way limit any subsequent procedures, or their effectiveness.

Embodiments of AIST involve accessing the tether so that a chemolysitic agent can be injected into the tether.

In one embodiment a method is disclosed, comprising: at each spinal segment (segmentally) drilling the lamina to allow access to the tether. This can be done percutaneously (through the skin) or by exposing one side of the lamina only (to preserve stability) to allow access to the lamina to drill the holes or perform small, unilateral (one side only) laminectomies. Each segmental tether is then injected with the chemolysitic agent through the access created. One such possible chemolysitic agent is collagenase *clostridium histolyticum*.

In another embodiment, the percutaneous drilling described above is performed using a drill that has an automatic stop. Various kinds of stops may be employed, including a mechanical stop that allows the drill to progress only to a pre-specified depth, or a drill which stops drilling automatically when the resistance on the drill bit changes (such as when it passes onto the other side of the bone). There are several different methods for constructing these kinds of drills. As described above, these methods can be applied percutaneously, e.g., using radiographic imaging or computer (or robot) assisted navigation. In some implementations employing a surgical robot, a mechanical stop may not be used for the drill as described above. The open surgical method would mean to access the tether through a unilaterally surgically exposed lamina.

In another embodiment, a method is disclosed, comprising: accessing a plurality of interspinous ligaments; and delivering at least one chemolysitic agent to the each of the corresponding plurality of interspinous ligaments via the multiple accesses created.

In another embodiment, a method is disclosed for treating adolescent idiopathic scoliosis, comprising: exposing a patient spine for a patient of age between 8 years and 19 years who is diagnosed with adolescent idiopathic scoliosis; drilling a plurality of vertebral laminae of vertebrae in a thoracic portion of the patient spine using a drill with automatic stop to provide access holes to each of a corresponding plurality of interspinous ligaments; and delivering collagenase *clostridium histolyticum* to the each of the corresponding plurality of interspinous ligaments via the access holes.

BRIEF DESCRIPTION OF THE DRAWINGS

The accompanying appendices and/or drawings illustrate various non-limiting, exemplary, innovative aspects in accordance with the present descriptions.

DETAILED DESCRIPTION

Figure 1A:
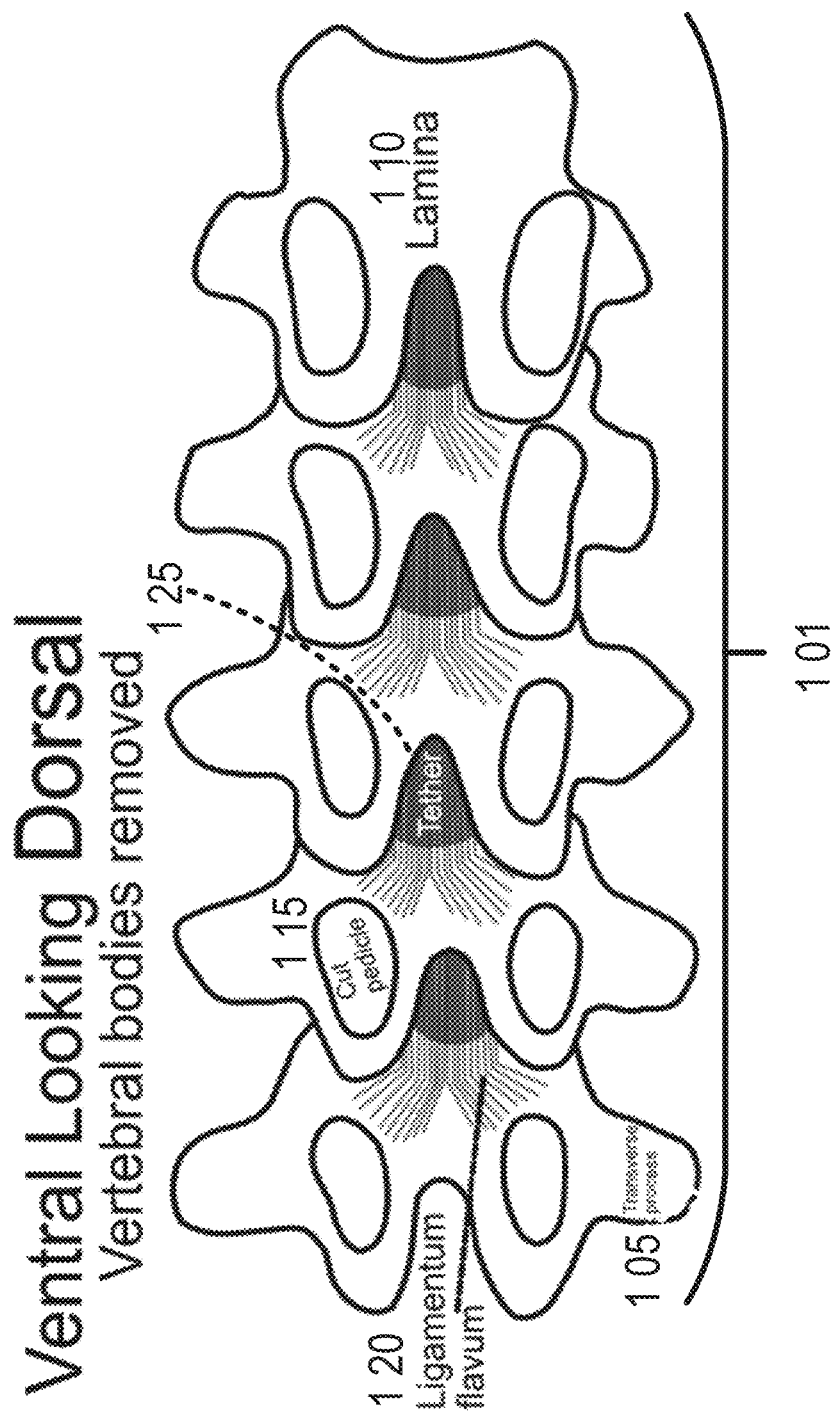
FIGS. 1A-1C show schematic views of a vertebral column in embodiments of the AIST.

The METHODS, APPARATUSES AND SYSTEMS FOR ADOLESCENT IDIOPATHIC SCOLIOSIS TREATMENT (hereinafter "AIST") disclosed herein leverage the biomechanical cause of AIS in the ventral portion of the interspinous ligament to treat AIS. In various embodiments, the AIST include chemically lysing the abnormal tethering structure, thereby allowing the AIS spine to decrease its deformity with usual day-to-day activities, without bracing and without instrumented and/or fusion surgery.

AIS is caused by a structure which is not normally present in the human spine. In patients with AIS, the base of the spinous processes on each vertebra are abnormally connected to the one above and below it (a segmental connection) by a tether which pathologically does not lengthen during growth. This tether is just posterior to the ligamentum flavum very near the spinal canal (where the nerves and spinal cord are). This tether (herein called "the tether") is the most ventral portion of the interspinous ligament. Normally this is an almost non-existent structure that is very weak and flimsy. However, in AIS patients, this tether is thick, heavy, and fibrous. When it is released it suddenly retracts about 2 millimeters, much like a guitar string which suddenly breaks. As the AIS adolescent grows, the anterior elements consisting primarily of the vertebral bodies grow more than the tethered posterior elements, which consist of the spinous processes, lamina, facets, spinal canal, transverse and spinous processes, and pedicles. The spine goes into extension as the anterior elements (vertebral bodies) continue growing unrestrained while the posterior elements are tethered, preventing them from lengthening during growth. The tether gets tighter and tighter like a piano string as the child continues to grow. Thus, in AIS the front of the spine is longitudinally long and the back of the spine is longitudinally short. The vertebral bodies are the primary load bearing structures of the spine and are significantly unloaded by the tether tilting the vertebral bodies backward. This makes the entire spinal column unstable.

The heart then pushes the vertebral bodies away which pop off to the side away from the heart, thus decreasing the tension on the tether and reducing toward normal the vertebral body loads. The vertebral bodies rotate around the tether. The tether remains straight because of the high tension it is under. Rotating away from the midline gives the vertebrae more room to grow. Because the vertebrae are no longer in the midline, the spine leans off to the side.

Thus, an abnormal ventral portion of the interspinous ligament acts as a biomechanical cause of AIS. This structure is a tether posterior to the spinal canal which does not accommodate normal growth. Thus the anterior aspect of the spine grows much faster than the posterior aspect. The posterior elements are held straight or nearly straight by the tether, while the anterior elements curve away from the midline, which gives them more space to grow.

The facets and ligamentum flavum are partially within the spinal canal and posterior to spinal cord. The tether lays on the ligamentum flavum (posteriorly), so that when the ligamentum is cut, the tether is cut also. There is no linkage currently in the literature between the improved deformity corrections and the biomechanical cause of AIS, or the tether contributing to the AIS deformity. Indeed, there is no recognition in the currently relevant literature of the existence of the tether at all, much less its location.

In about 1987, Dickson created adolescent-type scoliosis in rabbits by creating a tether and allowing the rabbits to grow. This model was so successful in creating anatomically accurate AIS that he subsequently attempted to release the tether by removing the bony posterior covering of the thoracic spine with wide decompressive laminectomies in patients. This had the effect of removing all of the posterior stabilizing structures of the spine. This included the supraspinous and interspinous ligaments, the muscles which no longer had the lamina to attach to, the bony mass of the lamina pushing up against the muscle fascia, skin, etc. With all of the posterior constraints gone, he had at least one patient (which he reported in the literature) whose spine collapsed forward, pinching the spinal cord, and causing complete paralysis. In order to safely release the posterior tether that causes AIS, the posterior constraining structures must be left mostly intact. The methods discussed herein consist of various methods for treating AIS by safely and segmentally (at each spinal level or between each vertebra) releasing the tether that is the root biomechanical cause of AIS.

Instead of laminectomy, which removes both sides of the vertebral bone and ligaments, which leaves the spine unstable, embodiments of the AIST employ chemolysis of the tether at multiple levels between two or more vertebrae thus preserving the critical stabilizing structures of the spine. The approach described herein is superior in many respects to previous treatments such as bracing, which does not correct AIS deformity, and actually by this model, may increase the AIS deformity. As discussed in further detail below, the biomechanical cause of AIS is the ventral portion of the interspinous ligament. This abnormal structure acts as a tether posterior to the spinal canal which does not accommodate normal growth. Thus the anterior aspect of the spine grows much faster than the posterior elements. The posterior elements are held straight or nearly straight by the tether, while the anterior elements curve away from the midline, which gives them more space to grow. In embodiments, by chemically lysing the abnormally tethering structure, the AIS spine decreases its deformity with normal day to day activities, without bracing, and without instrumented and/or fusion surgery. If subsequent instrumented (rods and screws) fusion surgery is desired, these methods do not prevent in any way further addressing the spine surgically. Because the tether is an abnormal structure which is not normally there, the loss of the tether will not affect the normal stability or stabilizing mechanisms of the spine.

A patient may be prepared for treatment by, for example, being administered anesthetic, shaving the skin surface, and/or the like. The posterior thoracic and or lumbar spines are surgically prepared with shaving and skin prep in the prone position. Sterile prep and drape may be applied. For percutaneous procedures, either local anesthetic or a combination of local anesthetic and sedation/general anesthesia can be used. Exposure of vertebrae and/or percutaneous incisions then allow for drill and/or needle access to the tether, e.g., under C-arm (x-ray) image or spine surgery robot control. Alternatively, under general anesthesia, a midline incision may be performed, and only one side of the fascia divided, and one side of the lamina exposed. In this procedure, a small window (unilateral laminotomy) is created to allow access to the tether at each exposed level. For the percutaneous methods, a drilling technique may be employed that halts drilling (e.g., by automatic stop) once the drill passes through the bone and reaches reduced resistance, or with a hard stop at a fixed depth. X-ray imaging could be used for these methods. A chemolysitic agent may then be applied to the tethers, such as by injection through the drilled access points in the vertebral laminae at each level that has been drilled. Such application of chemolysitic agent may be made, in various embodiments, without cutting or dissolving the ligamentum flavum, cutting bone (e.g., removing vertebral facets), and/or affixing rods or screws to the spine after the treatment procedure. In one implementation, chemolysitic agent may be applied at one or more vertebral levels along the spine (e.g., at all vertebral levels, at all thoracic vertebral levels, and/or the like). The number of levels to include may vary in different implementations. Various chemolysitic agents may be employed, e.g., to break down structural collagen or otherwise weaken tight soft-tissue structures in different implementations of the AIST. For example, in one implementation an enzyme such as collagenase *clostridium histolyticum* (currently available as Xiaflex, Xiapex, or generic *clostridium histolyticum*) or other collagenases may be employed. In some implementations, physical cutting of the tethers may be performed in addition to or instead of chemolysitic dissolution. Once the chemolysitic agent is applied, any incisions may be closed. The progress of the patient's condition (e.g., degree of spinal curvature) may be monitored and a determination made as to whether additional treatments are warranted. Otherwise, the treatment is completed.

In one embodiment, the above described procedure may be performed in children and/or adolescents prior to a growth spurt and up until substantial calcification of the tether occurs. For example, in one implementation, the procedure may be performed for patients older than 8 years old and younger than 19 years old. In another implementation, a determination may be made as to whether the procedure is suitable for a patient based on the patient's Risser sign (e.g., Risser sign between 1 and 3). In another embodiment, any person who still has flexibility in their spine would be a candidate for such treatments. Flexibility may be lost when the tether fuses or turns to bone, which is one way the body may seek to prevent the deformity from progressing more than minimally as the patient ages.

Figure 1B:
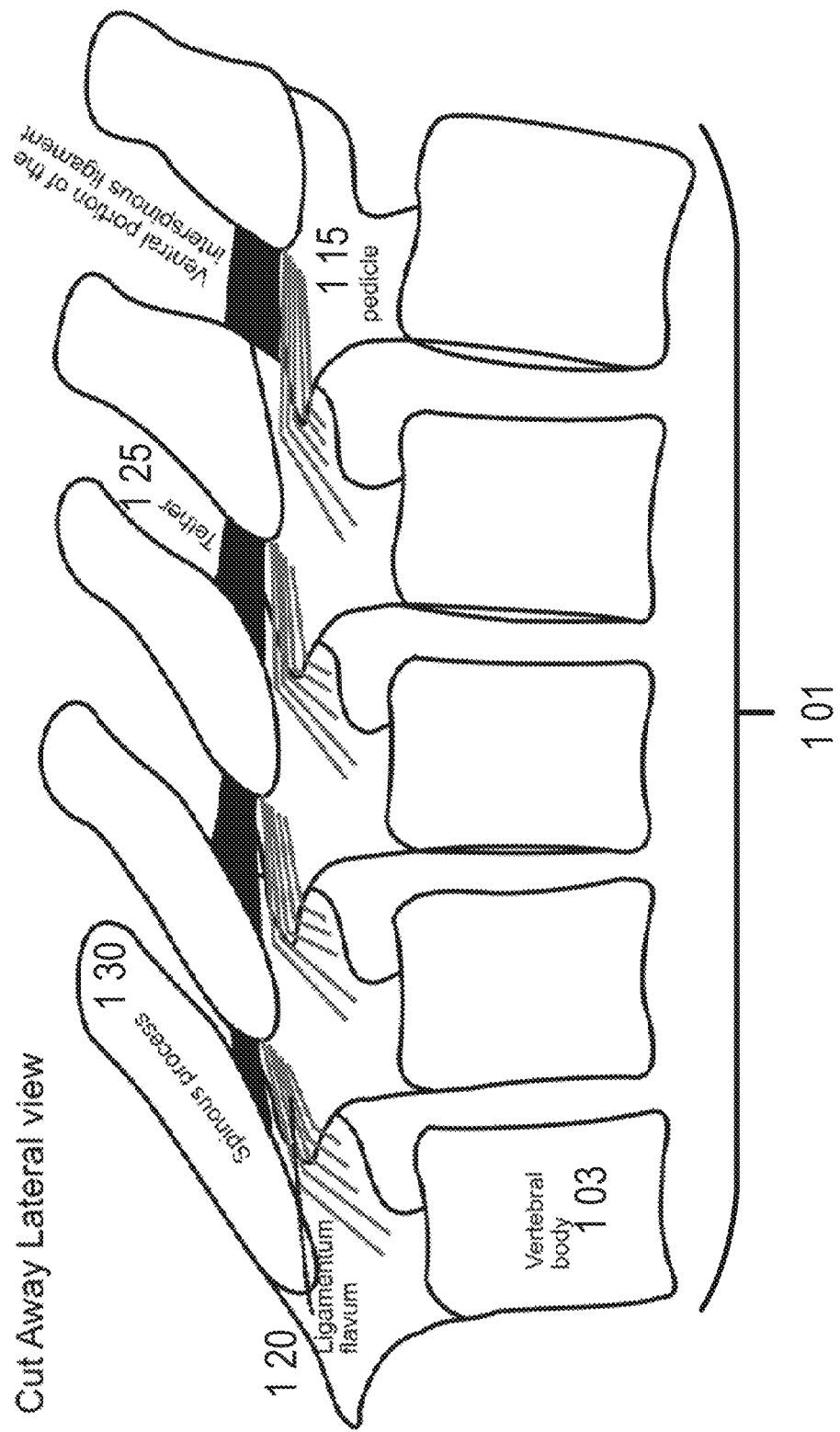
Figure 1C:
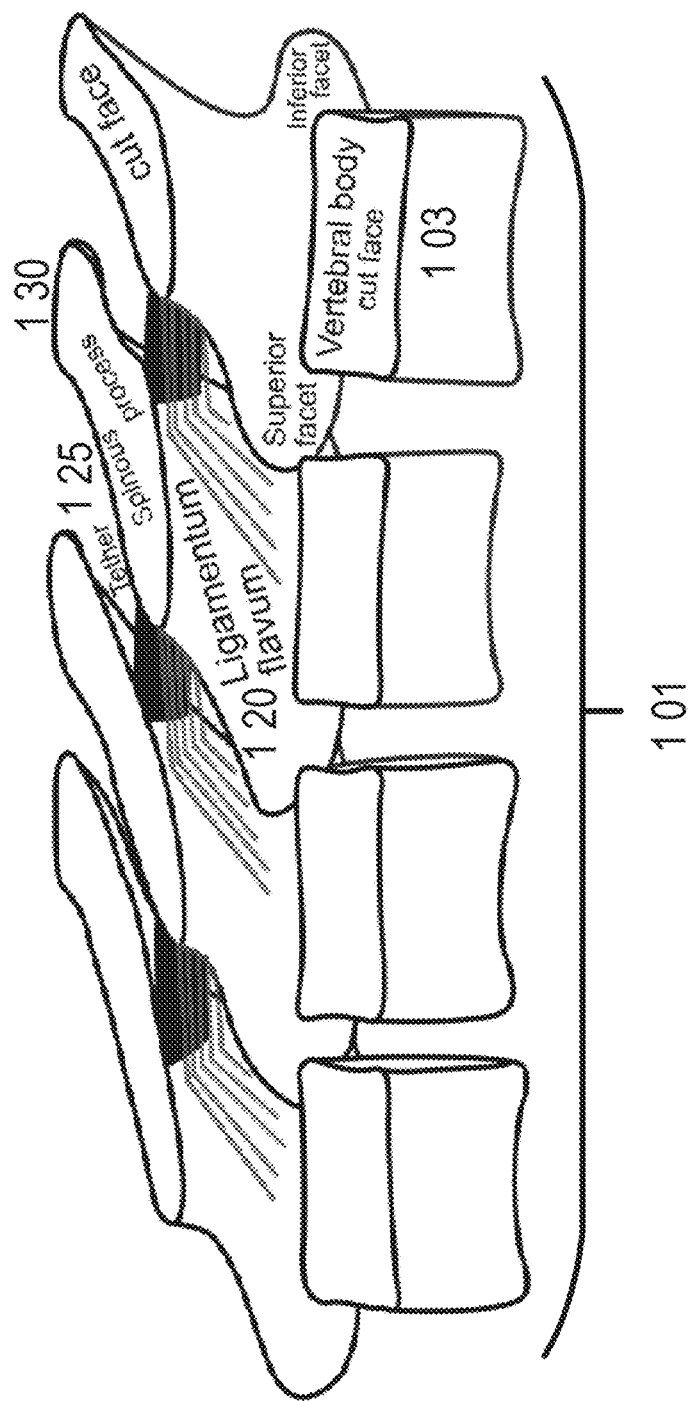

FIGS. 1A-1C show schematic views of a vertebral column in embodiments of the AIST. In FIG. 1A, a ventral (looking dorsal) view of the vertebral column is shown, with vertebral bodies removed for clarity of illustration (note that the vertebral bodies are not actually removed as part of the disclosed treatment). A plurality of vertebrae 101 comprising the vertebral column are shown, along with constituent elements thereof, including: the transverse process 105, vertebral lamina 110, pedicle (cut for clarity of illustration, not as part of the disclosed treatment) 115, ligamentum flavum 120, and the ventral portion of interspinous ligament or tether 125. The tether is the portion of the spinal column targeted by chemolysitic agent in embodiments of the AIST. The vertebral laminae 110 may be drilled to provide access to the tethers 125, e.g., for injection of one or more chemolysitic agents. FIG. 1B shows a cut-away lateral view of the vertebral column, again comprising a plurality of vertebrae 101. The vertebral body 103 and spinous process 130 are shown in this view, along with the pedicle 115, ligamentum flavum 120, and tether 125. FIG. 1C also shows a lateral view of the vertebral column, but with cut faces of the spinous process 130 and vertebral bodies 103 for further illustrative clarity (not cut as part of the disclosed treatment). Once again, the attachment of the ligamentum flavum 120 and tether 125 to the vertebrae 101 are shown.

Figure 2:
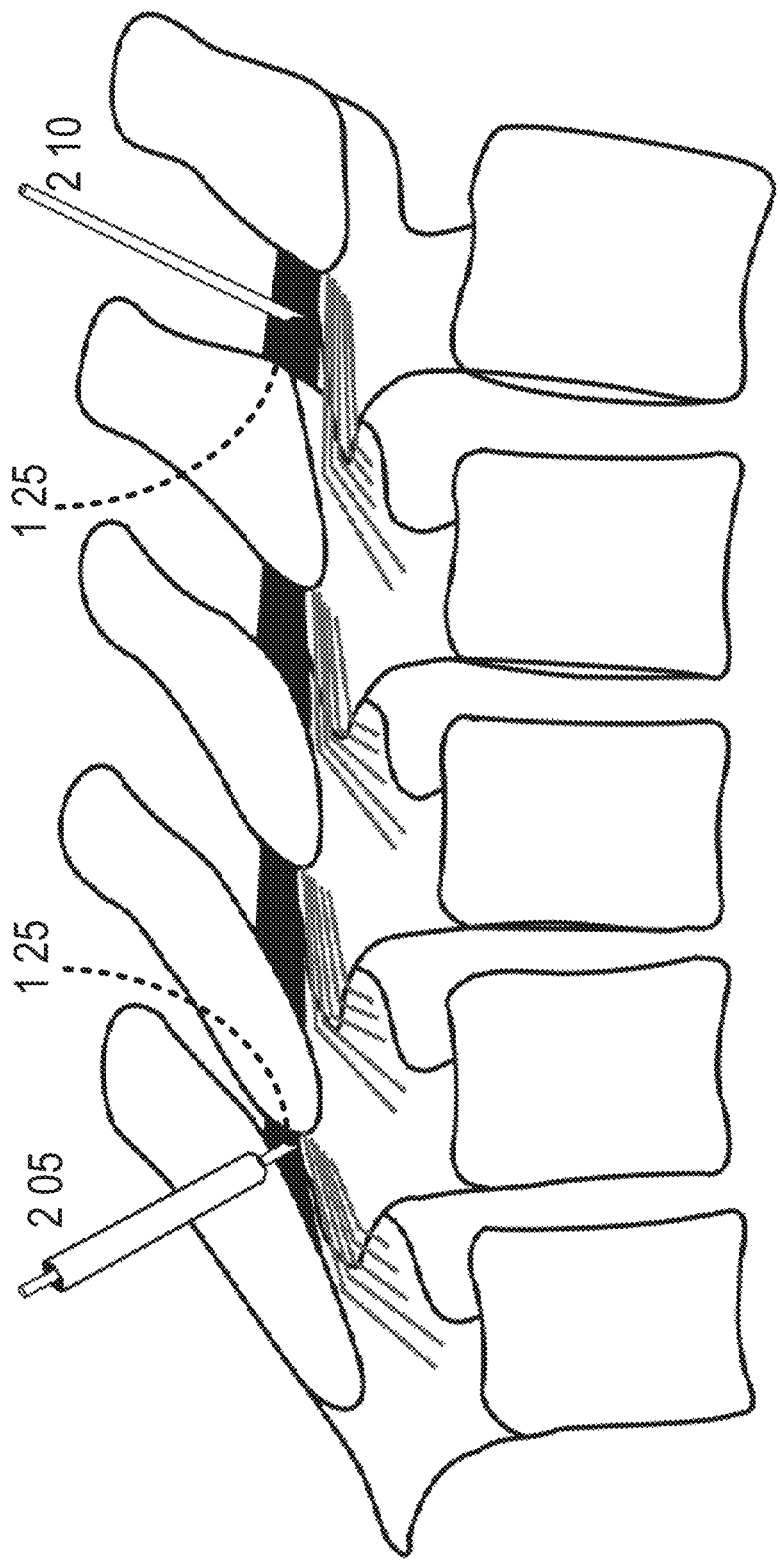
FIG. 2 shows cutting or dissolving of tethers in a lateral view of the vertebral column in embodiments of the AIST.

FIG. 2 shows cutting or dissolving of tethers in a lateral view of the vertebral column in embodiments of the AIST. An injection of chemolysitic agent 205 may be applied to tethers 125, such as via a hole drilled through the vertebral laminae. In addition, or alternatively, the tethers may be physically cut 210 in a targeted fashion (e.g., by a scalpel or similar instrument). With this process, the facets and posterior stabilizing structures of the spine are left intact.

Although primarily described herein in relation to the treatment of AIS, the disclosed embodiments of AIST may also be applied for the treatment of other disorders, particularly disorders involving uneven and/or distorted growth and/or structure of the spine. For example, embodiments of the AIST may be employed in the treatment of Scheuermann's disease, other postural kyphosis, or any other condition where there is a tether involved.

In order to address various issues and advance the art, the entirety of this application for METHODS, APPARATUSES AND SYSTEMS FOR ADOLESCENT IDIOPATHIC SCOLIOSIS TREATMENT (including the Cover Page, Title, Headings, Field, Background, Summary, Brief Description of the Drawings, Detailed Description, Claims, Abstract, Figures, Appendices, and otherwise) shows, by way of illustration, various embodiments in which the claimed innovations may be practiced. The advantages and features of the application are of a representative sample of embodiments only, and are not exhaustive and/or exclusive. They are presented only to assist in understanding and teach the claimed principles. It should be understood that they are not representative of all claimed innovations. As such, certain aspects of the disclosure have not been discussed herein. That alternate embodiments may not have been presented for a specific portion of the innovations or that further undescribed alternate embodiments may be available for a portion is not to be considered a disclaimer of those alternate embodiments. It will be appreciated that many of those undescribed embodiments incorporate the same principles of the innovations and others are equivalent. Thus, it is to be understood that other embodiments may be utilized and functional, logical, operational, organizational, structural and/or topological modifications may be made without departing from the scope and/or spirit of the disclosure. As such, all examples and/or embodiments are deemed to be non-limiting throughout this disclosure. Also, no inference should be drawn regarding those embodiments discussed herein relative to those not discussed herein other than it is as such for purposes of reducing space and repetition. For instance, it is to be understood that the logical and/or topological structure of any combination of any process steps and/or feature sets as described in the figures and/or throughout are not limited to a fixed operating order and/or arrangement, but rather, any disclosed order is exemplary and all equivalents, regardless of order, are contemplated by the disclosure. Similarly, some features are applicable to one aspect of the innovations, and inapplicable to others. In addition, the disclosure includes multiple innovations including some that may not be presently claimed, and the Applicant reserves all rights in those presently unclaimed innovations including the right to claim such innovations, file additional applications, continuations, continuations in part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the claims or limitations on equivalents to the claims.

What is claimed is:

1. A method for treating adolescent idiopathic scoliosis, comprising:
   drilling a plurality of vertebral laminae of vertebrae in a patient spine to provide access holes to each of a corresponding plurality of interspinous ligaments, wherein the drilling is performed percutaneously, and wherein the drilling includes, for each of the plurality of vertebral laminae, creating an access hole that terminates at a ventral portion of the respective interspinous ligament at a location posterior of the corresponding ligamentum flavum, without drilling through the ligamentum flavum;
   cutting at least a ventral portion of each of the corresponding plurality of interspinous ligaments; and
   delivering collagenase clostridium histolyticum to the each of the corresponding plurality of interspinous ligaments via the access holes.

2. The method of claim 1, wherein the plurality of vertebral laminae correspond to a thoracic portion of the patient spine.

3. The method of claim 1, wherein the patient spine corresponds to a patient of age between 8 years and 19 years.

4. The method of claim 1, wherein the drilling is performed using a drill with automatic stop.

5. A method for treating adolescent idiopathic scoliosis, comprising:
   exposing a patient spine for a patient of age between 8 years and 19 years who is diagnosed with adolescent idiopathic scoliosis;
   drilling a plurality of vertebral laminae of vertebrae in a thoracic portion of the patient spine to provide access holes to each of a corresponding plurality of interspinous ligaments, wherein the drilling is performed percutaneously, and wherein the drilling includes, for each of the plurality of vertebral laminae, creating an access hole that terminates at a ventral portion of the respective interspinous ligament at a location posterior of the corresponding ligamentum flavum, without drilling through the ligamentum flavum:
   cutting at least a ventral portion of each of the corresponding plurality of interspinous ligaments; and
   delivering collagenase clostridium histolyticum to the each of the corresponding plurality of interspinous ligaments via the access holes.

6. The method of claim 5, wherein the plurality of vertebral laminae are drilled using a drill with automatic stop.

7. A method for treating adolescent idiopathic scoliosis, comprising:
   at each of a plurality of spinal segments, segmentally drilling lamina to create an access hole allowing access to a corresponding segmental tether disposed within the interspinous ligament at a location posterior of the corresponding ligamentum flavum, without drilling completely through the interspinous ligament and without drilling through the ligamentum flavum, wherein the segmentally drilling lamina is performed percutaneously;
   cutting the segmental tether at each of the interspinous ligaments; and
   injecting collagenase clostridium histolyticum through the access holes to contact each segmental tether.

8. The method of claim 7, wherein the segmentally drilling lamina is performed using a drill having an automatic stop.

* * * * *